US012793839B1

(12) United States Patent
Grupp et al.

(10) Patent No.: US 12,793,839 B1
(45) Date of Patent: Nov. 10, 2026

(54) TRIAGE DEVICE WITH CARD READER

(71) Applicant: ZF Friedrichshafen AG, Friedrichshafen (DE)

(72) Inventors: Alexander Grupp, Tettnang (DE); Florian Müller, Rothenfels (DE)

(73) Assignee: ZF Friedrichshafen AG, Friedrichshafen (DE)

( * ) Notice: Subject to any disclaimer, the term of this patent is extended or adjusted under 35 U.S.C. 154(b) by 0 days.

(21) Appl. No.: 18/689,604

(22) PCT Filed: Aug. 9, 2022

(86) PCT No.: PCT/EP2022/072309
§ 371 (c)(1),
(2) Date: Mar. 6, 2024

(87) PCT Pub. No.: WO2023/036535
PCT Pub. Date: Mar. 16, 2023

(30) Foreign Application Priority Data

Sep. 8, 2021 (DE) ..................... 10 2021 209 895.9

(51) Int. Cl.
*G16H 40/20* (2018.01)
*G16H 10/65* (2018.01)

(52) U.S. Cl.
CPC ............ *G16H 40/20* (2018.01); *G16H 10/65* (2018.01)

(58) Field of Classification Search
CPC ............................... G16H 40/20; G16H 10/65
See application file for complete search history.

(56) References Cited

U.S. PATENT DOCUMENTS

| | | | | |
|---|---|---|---|---|
| 6,198,394 | B1 | 3/2001 | Jacobsen et al. | |
| 2008/0055074 | A1* | 3/2008 | Gao | A61B 5/0002 340/539.12 |
| 2010/0171611 | A1 | 7/2010 | Gao et al. | |
| 2013/0179185 | A1 | 7/2013 | Duffy et al. | |
| 2016/0005293 | A1* | 1/2016 | Yoo | G16H 40/67 340/539.11 |

(Continued)

FOREIGN PATENT DOCUMENTS

| | | | |
|---|---|---|---|
| DE | 10 2020 201 234 | A1 | 2/2021 |
| WO | 2006/077234 | A1 | 7/2006 |

OTHER PUBLICATIONS

European Patent Office, International Search Report issued for International application No. PCT/EP2022/07309 (Dec. 9, 2022).

(Continued)

*Primary Examiner* — Rachelle L Reichert
(74) *Attorney, Agent, or Firm* — Secant IP, P.L.L.C.

(57) ABSTRACT

The invention relates to a device (101) for registering a patient (303) in the event of an accident with multiple casualties and/or for locating a member of the emergency team (301). The device has at least one interface configured for a data-transmitting connection (310, 311, 313) between the device (101) and a data-processing device (305, 309). The device has at least one means (103) for attaching the device to the patient (303) or to the member of the emergency team (301), where the device (101) is designed to transmit an identifier by way of the data-transmitting connection (310, 311, 313). The device (101) is designed to read out the identifier from an identification means (203) of the patient (303) or the member of the emergency team (301).

7 Claims, 3 Drawing Sheets

(56) References Cited

U.S. PATENT DOCUMENTS

2016/0034479 A1* 2/2016 Skocic .................. G06Q 10/10
707/780

OTHER PUBLICATIONS

European Patent Office, Written Opinion issued for International application No. PCT/EP2022/07309 (Dec. 9, 2022).
Leslie A. Lenert et al., An Intelligent 802.11 Triage Tag for Medical Response to Disasters, AMIA 2005 Symposium Proceedings, pp. 440-445, https://www.ncbi.nlm.nih.gov/pmc/articles/PMC1560742/pdf/amia2005_0440.pdf.
German Patent Office, Office Action issued in German patent application No. 10 2021 209 895.9 (May 10, 2022).

* cited by examiner

TRIAGE DEVICE WITH CARD READER

RELATED APPLICATIONS

This application claims the benefit under 35 U.S.C. § 371 as a U.S. National Phase Application of application no. PCT/EP2022/072309, filed on 9 Aug. 2022, which claims the benefit of German Patent Application no. 10 2021 209 895.9 filed on 8 Sep. 2021, the contents of which are hereby incorporated herein by reference in their entireties.

FIELD OF THE DISCLOSURE

The invention relates to a triage device with card reader.

BACKGROUND

From the prior art, so-termed injury attachment cards are known. In the event of an accident with multiple casualties, these serve to classify the patients who require care. An injury attachment card is attached to each patient. It contains a colored field whose color indicates the patient's condition. The patient's condition is assigned by the emergency services to one of several categories, known as triage categories. Each triage category is associated with a particular color of the injury attachment cards.

US20100171611 A1 and DE 10 2020 201 234 A1 disclose digital, network-supported triage systems. In each case, injury attachment cards are implemented in the form of electronic devices. The devices have in each case a display means which indicates the triage category of the patient concerned. By way of a wireless network connection the devices are connected to a central computer or a Cloud. The devices can be coupled to measurement means for the vital functions of the patient. For identification purposes each device is provided with an ID.

SUMMARY

The purpose of the present invention is to improve the registration of patients in the event of an accident with multiple casualties and the location of the emergency services. This objective is achieved by a triage device and method as disclosed herein. Preferred further developments are described and will be apparent from the figures and the description given below.

The device according to the invention serves to register a patient in the event of an accident with multiple casualties and/or the location of the emergency services. An accident with multiple casualties (MANV) denotes a situation in which a large number of those concerned are in need of care.

The device is provided with at least one interface for data-transmitting connection between the device and a data-processing device. The data-transmitting connection is preferably of the wireless type.

As the data-processing device, a central, fixed-location device can be considered, which for example can be designed as a Cloud, i.e., an association of a plurality of data-processing devices interconnected by means of data-transmitting connections. The data-processing device can also be a mobile terminal device, or a further data-processing device embedded in an emergency vehicle. For example, the mobile terminal device is used by an emergency service and, for its part, is connected to the fixed device.

The device according to the invention comprises at least one means for attaching the device to a patient or to a member of the emergency team. The means, for example, can be a strap by which the device is hung around the neck of the patient or member of the emergency team. The means can also be in the form of a clip by which the device is attached to the clothing of the patient or member of the emergency team.

When the device is attached to the patient or to a member of the emergency team, a position of the device matches a position of the patient or member of the emergency team. Since the device is located, so too is the patient or member of the emergency team.

The device is designed to transmit an identifier via the data-processing device. An identifier is a feature linked to a specific identity for the unambiguous identification of an object or a person. Thus, the linking of identifiers to the objects or persons to be identified constitutes an objective relationship.

The invention provides identification means for the patient and/or the member of the emergency team. An identifier of the patient or member of the emergency team concerned is stored on the identification means.

According to the invention, the device is designed to read out the identifier of the patient to be registered or the member of the emergency team to be located from the identification means concerned. Thus, according to the invention, the identification of the patient and/or the member of the emergency team takes place not by way of an identifier of the device, but rather by virtue of a person-specific identifier which is stored in an identification means. This improves the accuracy of the association between the identifier and the person to be identified. In particular, person-specific data can be associated with the identifier.

The identifiers can be stored and read out, for example, by means of NFC or RFID.

Preferably, the device is developed further with a retaining device for the identification means. The retaining device serves to hold and attach the identification means. This implies that the identification means can be inserted into the retaining device. In the inserted condition, the identification means is held fixed by the retaining device. The fixing of the identification means in the retaining device is preferably releasable so that, if necessary, the identification means can be taken out of the retaining device.

Preferably, the identification means is in the form of a card. In that case a suitable retaining device is a slot with a card reader into which the card can be inserted.

DE 10 2020 201 234 A1 describes further preferred features of the device. Accordingly, the content of DE 10 2020 201 234 A1 is referentially included herein.

A method according to the invention serves to register a patient in the event of an accident with multiple casualties. According to the invention, the device according to the invention or a preferred further development thereof is attached to the patient. This is done using the means described earlier.

The method provides that an identifier of the patient is stored in an identification means. By means of the device, the identifier is read from the identification means. For the identification of the patient an identification document or a health insurance card can be considered.

A further method according to the invention is carried out analogously to the location of a member of the emergency team. Using the means for fixing the device described earlier, the device is attached to the member of the emergency team to be located. The method provides that an identifier of the member of the emergency team is stored on an identification means. The identifier is read by the device. In this case, too, an identification document is suitable as the identification means. Likewise, a service card can serve to identify the member of the emergency team.

BRIEF DESCRIPTION OF THE DRAWINGS

Preferred example embodiments of the invention are illustrated in the figures, which show, in detail.

DETAILED DESCRIPTION

Figure 1:
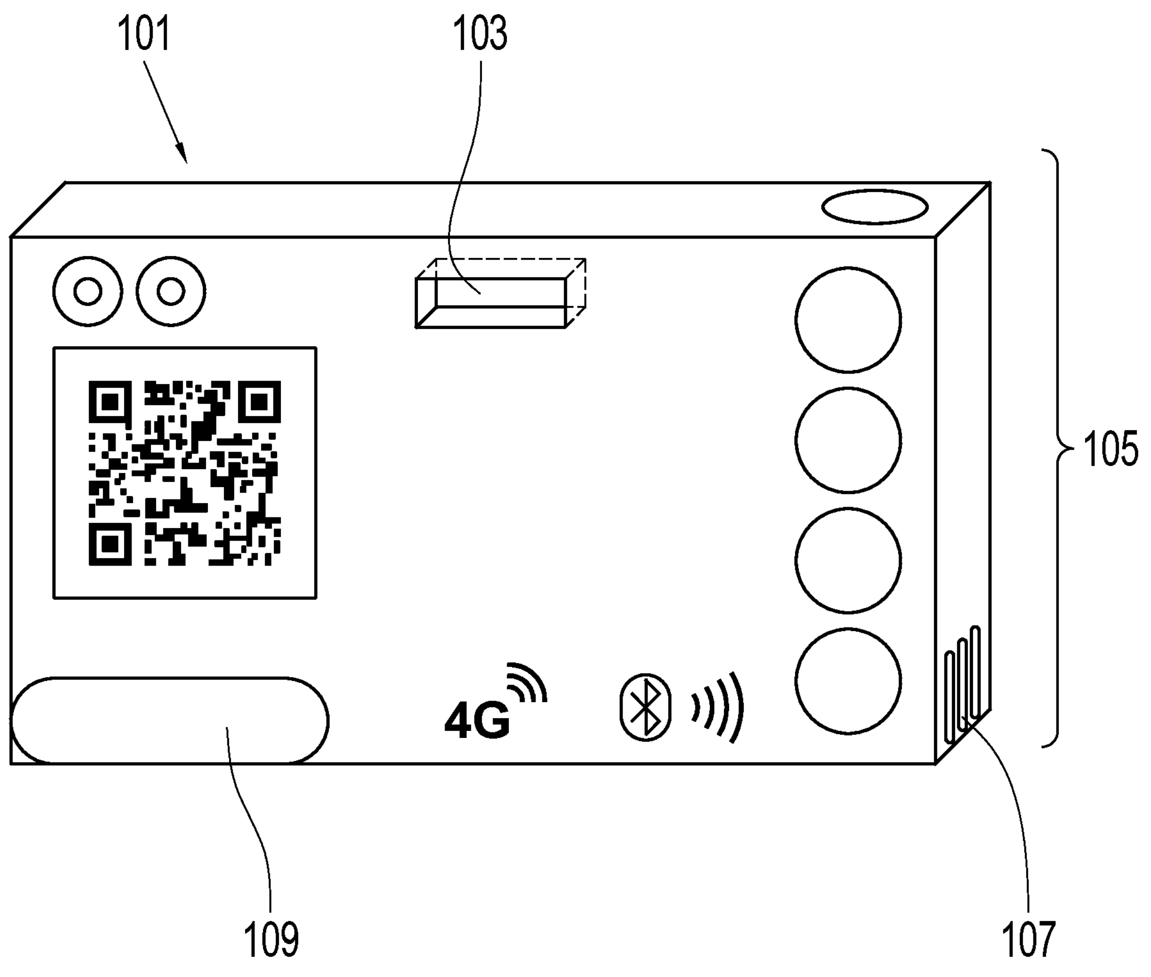
FIG. 1: A front view of a device.
Figure 2:
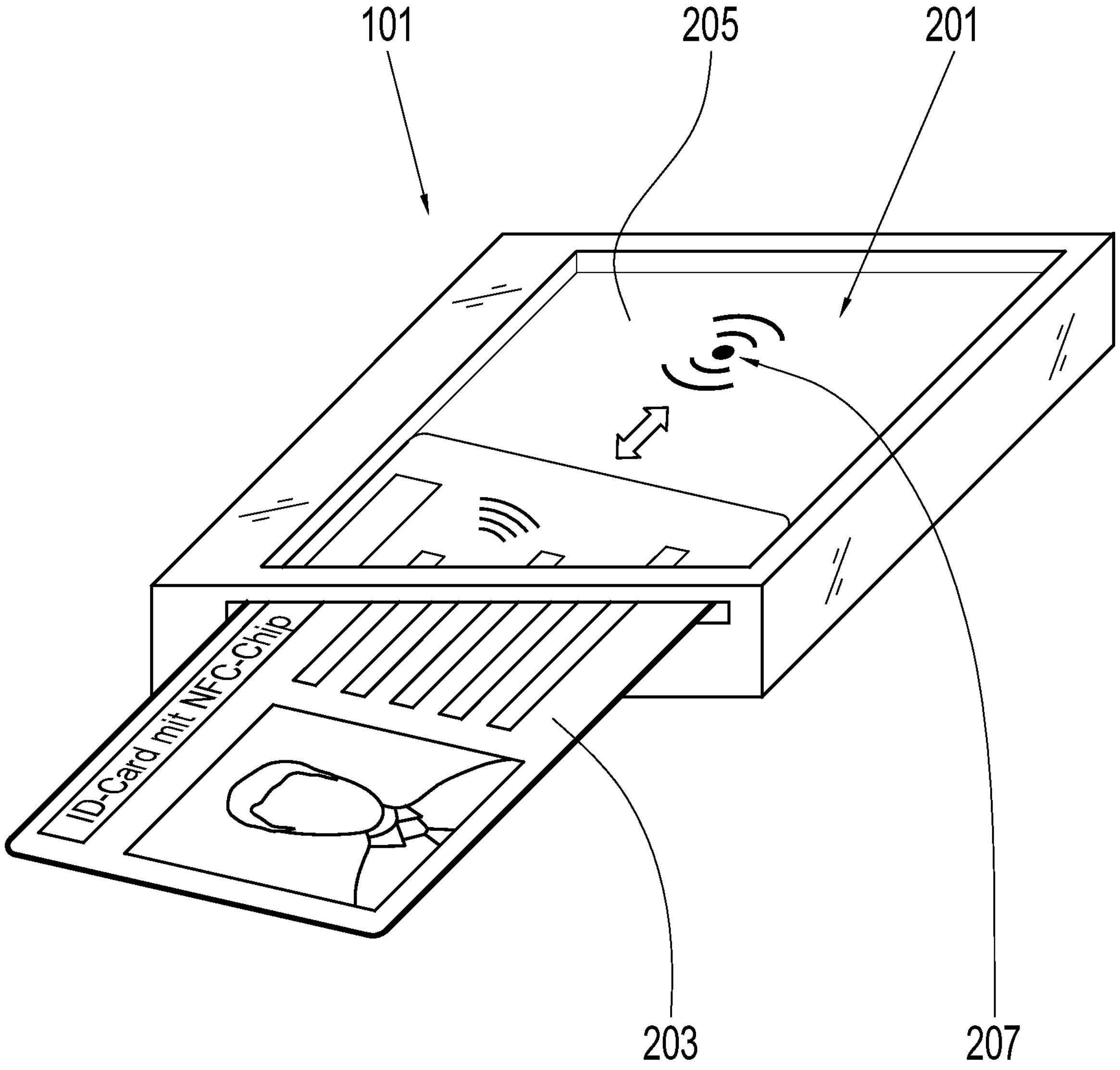
FIG. 2: A rear view of the device.

The device 101 shown in FIGS. 1 and 2 can be used optionally for registering a patient or for locating a member of the emergency team in the event of an accident with multiple casualties. To register a patient the device 101 is attached to the patient by a rescuer. This is done for example by means of a strap or a clip. To attach the strap or clip to the device 101, the device 101 has an opening 103.

A triage category of the patient can be selected by way of an input element 105. As the input element, a panic-button can also be provided. When the panic-button is pressed an alarm is triggered. In that way help can be called for, for example when a member of the emergency team has reached the site of an emergency. In that case an acoustic alarm signal is emitted by a loudspeaker.

A light element serves to indicate the triage category. The light element 109 changes its color as a function of the triage category selected by the input element 105.

On the opposite side shown in FIG. 2, the device 101 comprises a card reader 201. The card reader 201 is in the form of a slot into which an ID card 203 of a patient or a member of the emergency team can be inserted. So that the ID card 203 remains visible when inserted, the slot of the card reader 201 has a transparent cover 205. In the card reader 201 there is a NFC or RFID reader unit 207. By means of the reader unit 207 the data stored on the ID card 203 can be read.

Figure 3:
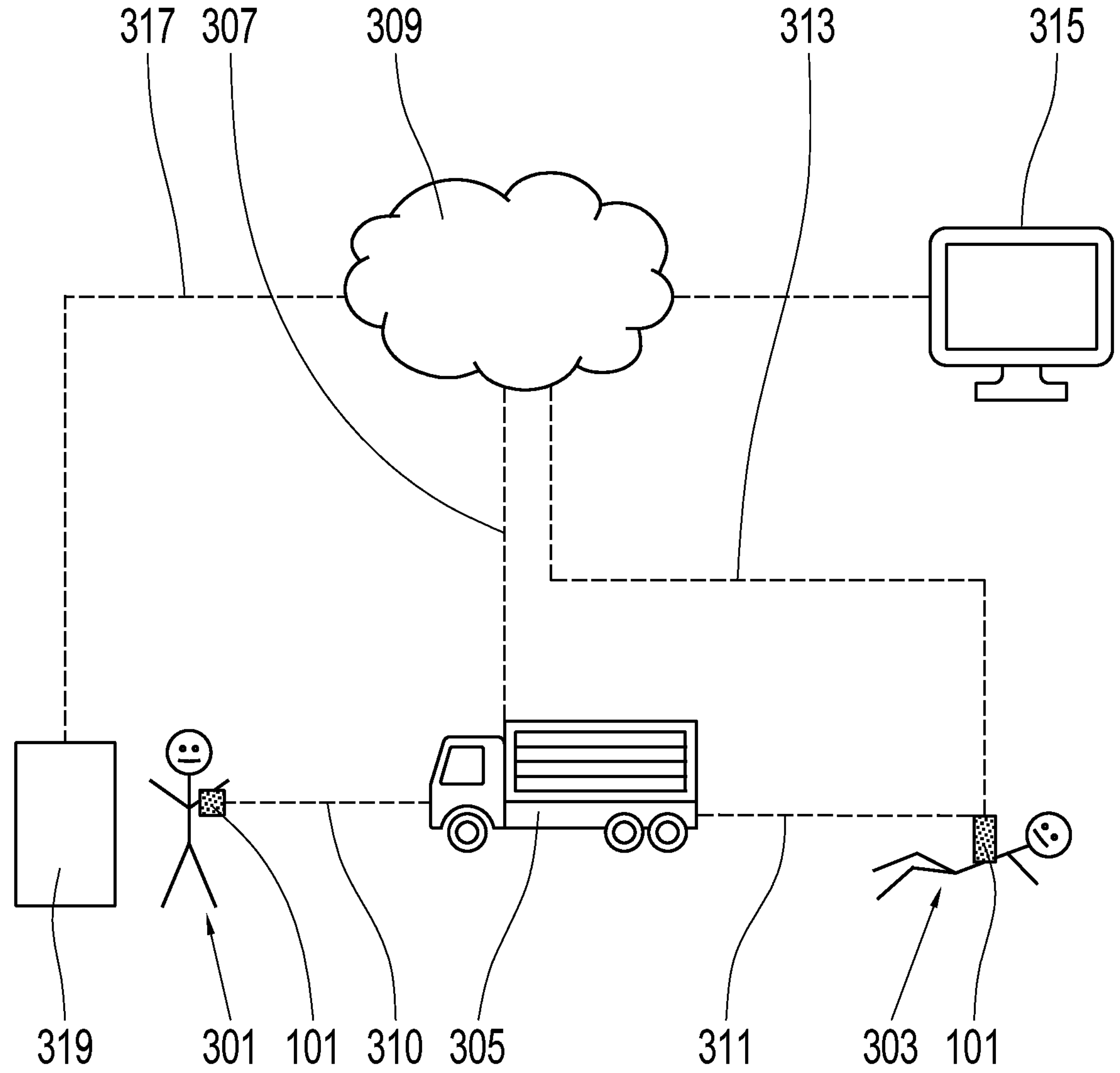
FIG. 3: An overall view of a system.

FIG. 3 shows two of the units of the device 101 involved in the triage system. In this case a member of the emergency team 301 and an injured person 303 both carry such a device 101.

An emergency vehicle 305 is integrated in the system by way of a data processing unit of its own. Thus, the data processing unit of the emergency vehicle 305 is connected with a Cloud 309 via a data-transmitting connection 307.

The devices 101 are connected via further data-transmitting connections 310, 311 to the data-processing unit of the emergency vehicle 305. The data-processing unit of the emergency vehicle 305 functions as a router by way of which a connection of the respective device to the Cloud 309 is created. Compared with a direct connection this is advantageous, since the emergency vehicle 305 is in the immediate vicinity and the data-transmitting connection 110 to the emergency vehicle 305 is therefore better available and more stable.

Alternatively, the device 101 of the injured person can be connected directly to the Cloud 309 via a data-transmitting connection 313. A direct connection is necessary if no emergency vehicle is yet on site.

The data of the emergency services 101 and the injured person 303 collected in the Cloud 309 are collected in an operational control center 315 and evaluated for the purpose of coordinating the operation. Furthermore, it is possible, by way of a data-transmitting connection 317 between the Cloud 309 and a mobile terminal device 319, to send the data to the emergency services on the spot.

Moreover, the devices 101 and 201 can be used to transmit vital data of the injured person 303 to the member of the emergency team 101. In particular it is possible to transmit the data to the Cloud 309 so that the data can be taken into account during the planning of the rescue operation. By transmitting the vital data any deterioration in the health condition of the injured person 303 can be recognized directly. If there is any deterioration of the vital functions of the member of the emergency team 101, further emergency services can be brought in.

The vital functions are detected by means of special instruments, for example by so-termed Smartwatches. These instruments form part of a short-range network in which the device 101 of the member of the emergency team 101 and the device 201 of the injured person 303 are also included.

INDEXES

101 Device
103 Opening
105 Input element
107 Loudspeaker
109 Light element
201 Card reader
203 ID card
205 Cover
207 Reader unit
301 Member of the emergency team
303 Person
305 Emergency vehicle
307 Data-transmitting connection
309 Cloud
310 Data-transmitting connection
311 Data-transmitting connection
313 Data-transmitting connection
315 Operational control center
3'7 Data-transmitting connection
319 Mobile terminal device

The invention claimed is:

1. A method for registering a patient in the event of an accident with multiple casualties, the method comprising:

providing a device configured for registering a patient, the device comprising:

at least one interface configured for a wireless data-transmitting connection between the device and a data-processing unit of an emergency vehicle;

a panic button configured that, when depressed, triggers an alarm; and at least one means for attaching the device onto a patient or a member of the emergency team;

wherein the device is configured to wirelessly transmit a person-specific identifier via the wireless data-transmitting connection, wherein the person-specific identifier is stored in the device;

wherein the device is configured to read out the person-specific identifier of the patient or the member of the emergency team; and a light element on the device, the light element configured to emit a plurality of light colors each indicative of a triage category of the patient;

attaching the device to the patient;

reading, by the device, the person-specific identifier of the patient from an identification means of the patient;

emitting an alarm signal from the device; and emitting an acoustic alarm via a loudspeaker in response to the emitted alarm signal.

2. The method according to claim 1, wherein the device comprises a releasable retaining device on the person-specific identifier.

3. A method for coordinating a response to an accident with multiple casualties, the method comprising:

providing a plurality of devices each configured for registering a patient and comprising:

at least one interface configured for a wireless data-transmitting connection between the device and a data-processing unit of an emergency vehicle;

a panic button configured that, when depressed, triggers an alarm; and at least one means for attaching the device onto a patient or a member of the emergency team;

wherein the device is configured to wirelessly transmit a person-specific identifier via the wireless data-transmitting connection, wherein the person-specific identifier is stored in the device;

wherein the device is configured to read out the person-specific identifier of the patient or the member of the emergency team; and a light element on the device, the light element configured to emit a plurality of light colors each indicative of a triage category of the patient;

attaching a first device of the plurality of devices to the member of the emergency team;

attaching a second device of the plurality of devices to the patient;

reading in, by the first device, the person-specific identifier of the member of the emergency team from an identification means of the member of the emergency team;

reading in, by the second device, the person-specific identifier of the patient;

wirelessly connecting the plurality of devices to an operational control center;

collecting, by the operational control center, data of the patient and of the member of the emergency team;

emitting, by the light element on the second device, a light color indicative of a triage category of the patient; and coordinating the response to the accident based on the data collected.

4. The method according to claim 3, comprising:

transmitting vital data of the patient to the member of the emergency team.

5. The method according to claim 4, comprising:

transmitting vital data of the patient to the operational control center;

determining, by the operational control center, a change in the vital data of the patient; and changing, by the operational control center, the light color of the light element on the second device.

6. The method according to claim 3, comprising:

emitting an alarm signal from the second device; and emitting an acoustic alarm signal via a loudspeaker in response to the alarm signal.

7. The method according to claim 3, wherein each device of the plurality of devices comprises a releasable retaining device on the person-specific identifier.

* * * * *